United States Patent [19]

Stauffer et al.

[11] Patent Number: 4,825,880
[45] Date of Patent: May 2, 1989

[54] IMPLANTABLE HELICAL COIL MICROWAVE ANTENNA

[75] Inventors: Paul R. Stauffer, San Rafael; Toru Satoh, San Francisco, both of Calif.

[73] Assignee: The Regents of the University of California, Berkeley, Calif.

[21] Appl. No.: 64,334

[22] Filed: Jun. 19, 1987

[51] Int. Cl.⁴ .............................................. A61N 5/02
[52] U.S. Cl. .................................... 128/804; 128/401; 128/784
[58] Field of Search .................... 128/804, 784, 401

[56] References Cited

U.S. PATENT DOCUMENTS

| | | | |
|---|---|---|---|
| 4,154,246 | 5/1979 | LeVeen | 128/804 X |
| 4,583,556 | 4/1986 | Hines et al. | 128/804 |
| 4,658,836 | 4/1987 | Turner | 128/804 |
| 4,712,559 | 12/1987 | Turner | 128/804 |

FOREIGN PATENT DOCUMENTS

| | | | |
|---|---|---|---|
| 0105677 | 4/1984 | European Pat. Off. | 128/804 |
| 1266548 | 10/1986 | U.S.S.R. | 128/804 |

*Primary Examiner*—Lee S. Cohen
*Attorney, Agent, or Firm*—Phillips, Moore, Lempio & Finley

[57] ABSTRACT

An implantable helical coil microwave antenna, particularly adapted for interstitial hyperthermia therapy of cancer, comprises a coaxial cable having a distal end of its outer conductor removed and a helical coil mounted on the exposed inner conductor insulator. A proximal end of the helical coil is separated axially from the distal end of the outer conductor and the distal end of the helical coil is connected to the inner conductor of the coaxial cable feed line. The antenna functions to confine heat to the area immediately surrounding the coil and thus induces substantially identical thermal profiles at varying antenna insertion depths in tissue when the antenna is energized with microwave energy.

12 Claims, 3 Drawing Sheets

IMPLANTABLE HELICAL COIL MICROWAVE ANTENNA

This invention was made with Government support under Grant Contract No. CA-39428 and CA-13525 awarded by the National Institute of Health. The Government has certain rights in this invention.

TECHNICAL FIELD

This invention relates generally to a microwave antenna and more particularly to an implantable helical coil microwave antenna for improved localization of interstitial hyperthermia.

BACKGROUND ART

Hyperthermia constitutes an effective adjuvant treatment for malignant tumors which are refractory to conventional therapy with surgery, radiation or chemotherapy. Hyperthermia can be administered to a patient either by an externally applied electromagnetic or ultrasound source, or internally by an interstitial heating technique. Implantable microwave antenna heating has proven the most popular of the three present interstitial heating modalities.

However, major problems arise with the use of conventional half-wavelength dipole antennas which severely limit the applicability and effectiveness of interstitial microwave hyperthermia. Such problems include: variability of heating profiles when the antenna is inserted to different depths in the tissue to be treated, restricted range of possible heating lengths for a given microwave frequency, and the presence of a so-called "cold region" or "dead length" occurring at the tip of the antenna. Attempts have been made to solve one or more of the above problems by providing implantable radiating antennas having improved performance characteristics.

For example, two-node and three-node microwave antennas have been proposed to expand the heating volume to as much as twice that provided by a single-node dipole antenna. However, such antennas have exhibited an inhomogenous heating pattern with three or four peaks along the antenna axis and a failure to heat effectively out of the antenna tip. A variable diameter dipole antenna has also been proposed to force the heating current into larger diameter sections of the antenna which fit snugly within the biocompatible plastic catheter. The larger diameter section at the tip of the antenna appears to provide more effective tip heating, but the antenna still exhibits considerable dependence of heating on insertion depth and periodic excessive surface tissue heating.

Other types of dipole antennas, such as the sleeved coaxial slot and balun-fed folded dipole, have been proposed for shifting the heating field out to the antenna tip. The concept of multiple breaks in the coax outer conductor of the antenna with each section being driven by a separate microwave source has held some promise for closer control of the depth heating profile, but at the expense of greatly increased equipment complexity. Although often accomplishing an expansion of the effective heating length for a given frequency and/or a reduction in dead length at the tip, the above types of antennas are commonly plagued with the same critical problem as that of the linearly polarized simple dipole antenna, namely, a critical dependence of the heating pattern on the depth of insertion.

Another proposed technique employs an "over-ride" reciprocated motion system for linearly translating the dipole antenna during treatment. Although this technique may potentially solve at least part of the axial heating pattern problem, predictability and real time control of the overall heating pattern would likely prove difficult due to power deposition pattern changes at different positions within the range of antenna movement.

A similar development of antenna designs has occurred for intracavitary heating applications. Antennas of this type having somewhat larger diameters (e.g., 1-1.5 cm v. 0.1-0.15 cm) have been used in the treatment of tissues surrounding body cavities. An antenna of the latter type has been constructed with a 1.0 cm diameter coax cable outer conductor cut in a helical manner and pulled apart axially to form a helical extension of the antenna feedline outer conductor having ten turns extending 14 cm in length. Thermal profiles of the antenna were found to be quite variable for the different conditions studied and the antenna exhibited a strong dependence on both source frequency and insertion depth. Most tests were performed using insertion depths less than the 14 cm length coil.

A so-called "flexible leakage type" antenna has also been proposed for use at 2450 MHz. This type of antenna consists of a helical structure composed of 1.0 mm wide copper foil tape interconnected between the inner and outer conductors of a 2.0 mm diameter flexible coaxial cable.

DISCLOSURE OF THE INVENTION

The improved microwave antenna of this invention is comprised of an inner conductor, a dielectric insulator covering the inner conductor and an outer conductor covering only a proximal portion of the insulator to form a coaxial cable thereat and to leave a distal portion of the insulator uncovered. A helical coil surrounds the distal portion of the insulator and has its proximal end spaced axially from a distal end of the outer conductor and its distal end connected to a distal end of the inner conductor.

The antenna will function to confine heat to the immediate area surrounding the helical coil and to produce substantially identical thermal profiles at varying depths of insertion of the antenna into the treatment volume tissue when the antenna is energized with microwave energy. In addition, the antenna of this invention exhibits other advantages over existing implantable microwave antenna designs. For example, the size of the heated volume for a given frequency can be adjusted readily by simply changing the length of the coil (within a preselected range). The dead length (cold portion at the end of the implanted antenna) is eliminated which minimizes the need for implanting antennas deeper than the lower extent of the target region. Undesirable tissue heating along the antenna feedline is eliminated with deep insertions, as well as overheating of the tissue surface for shallow depth insertions of the antenna.

The antenna of this invention will thus provide well focused and controlled interstitial hyperthermia to a given volume of tissue, regardless of location within a larger structure without undesirable and uncontrollable hot spots along the antenna feedline. Multiple antenna arrays may be used to expand the effective heating volume laterally, using either coherently or incoherently phased microwave sources. Use of the antenna is compatible with existing radioactive seed brachytherapy for combination interstitial hyperthermia and radiation therapy of malignant tumors. Although the antenna is particularly adapted for improved heating uniformity in interstitial hyperthermia therapy of cancer, the antenna is useful for a variety of other applications wherein heat must be applied uniformly to the interior of large lossy dielectric volumes. New applications in food warming, material quick-thawing and tissue therapy are expected with reduced pricing of antennas and microwave sources.

BRIEF DESCRIPTION OF THE DRAWINGS

Other objects and advantages of this invention will become apparent from the following description and accompanying drawings wherein.

BEST MODE OF CARRYING OUT THE INVENTION

General Description

Figure 1:
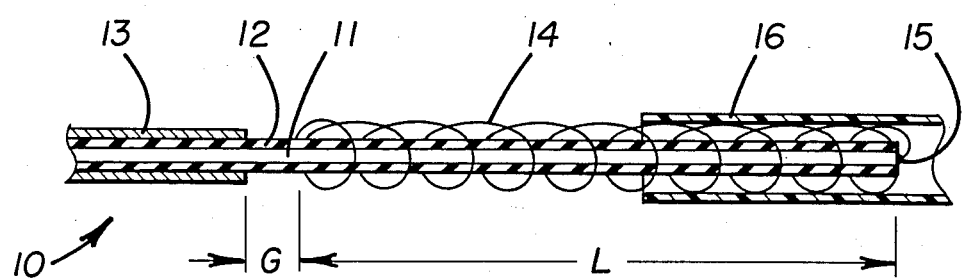
FIG. 1 is a longitudinal cross-sectional view of a microwave antenna embodying this invention.

FIG. 1 illustrates an implantable helical coil microwave antenna 10 embodying the present invention. The antenna was constructed from a miniature coaxial cable comprising a metallic inner conductor 11 surrounded by a tubular dielectric insulator 12 fully covering the inner conductor. A distal section of a tubular metallic outer conductor 13 was removed so that the outer conductor only covered a proximal portion of insulator 12 to form a coaxial cable portion thereat and to leave a distal portion of the insulator uncovered.

A metallic wire helical coil 14 was constructed to surround the distal portion of insulator 12 and to have its proximal end spaced axially from a distal end of outer conductor 13 to form a separation gap G therebetween. A distal end of the helical coil was soldered and connected at 15 to a distal end of inner conductor 11. As more fully explained hereinafter, antenna 10 was found to confine heat to the immediate area surrounding helical coil 14 and to induce substantially identical thermal profiles at varying depths of insertion of the antenna into an organic subject when the antenna was energized with microwave energy.

In use, antenna 10 is adapted to slip within a standard 16-gauge plastic catheter 16, as is, commonly used for brachyradiotherapy treatments. In use, the catheter entirely covers the implanted antenna and is closed at is distal end. Antenna design parameters, such as the axial coil length L, coil turn density and specific wire material composing helical coil 14, are predetermined for proper impedance match to biological tissue at a given microwave frequency.

The exact number of coil turns and separation distance of gap G are predetermined for each antenna application, along with the coil turn density and connection configuration of the coil to the coax feed line which are essential determinates of the radiated field. In addition to the ability of antenna 10 to effectively confine heat to the region immediately surrounding helical coil 14 and to efficiently radiate such heat independently of implanted depth, the size of the heated voluem can be readily adjusted by adding more such antennas to the array, by changing frequency and/or by changing length L of the helical coil for a given coil turn density. Additional adjustments to the heating field may be accomplished by using variable spacing and variable diameter of the coil turns to shape the power deposition pattern along the antenna length. Since the dead length (cold portion at the end of the implanted antenna) is eliminated, the need for implanting the antenna deeper than the lower extent of the target region is minimized. Also, undesirable tissue heating along the antenna feedline is eliminated along with overheating of the tissue surface for shallow depth insertions.

Figure 2:
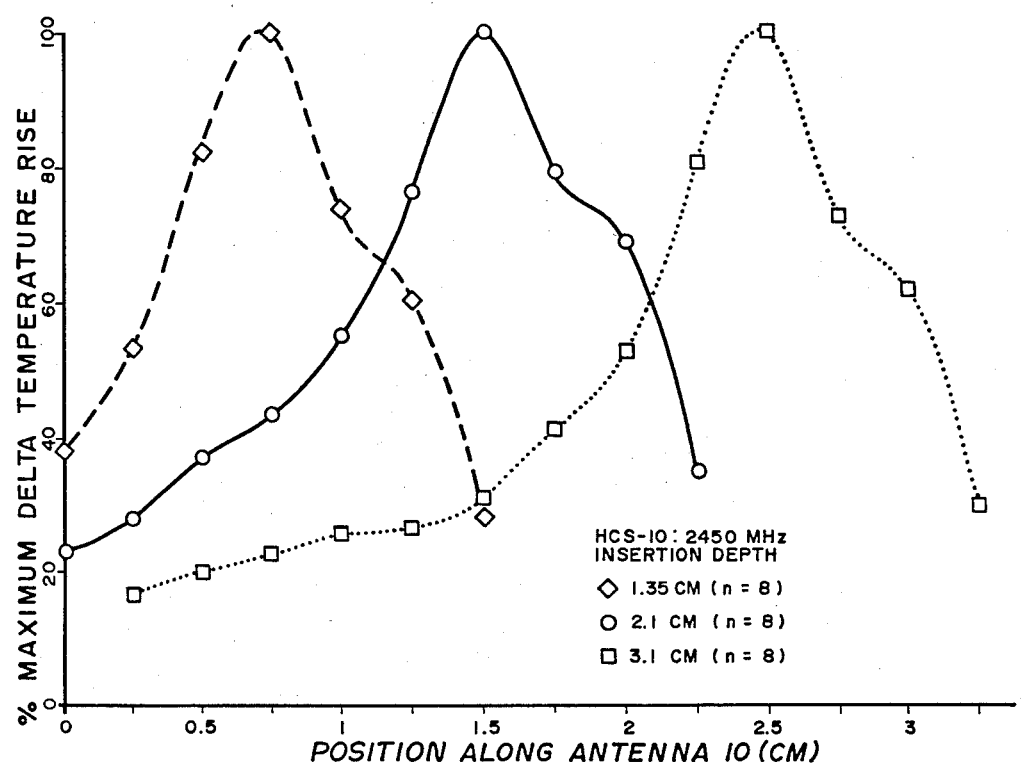
FIG. 2 graphically illustrates the effect of varying insertion depths on the axial thermal profiles of a 2450 MHz, L=1 cm. helical coil antenna in a tissue equivalent homogenous phantom.

Comparative testing of antenna 10 against the simple dipole antenna 17 (FIG. 3) showed that the power deposition characteristic of the standard antenna varied significantly for varying insertion depth (FIG. 4) in contrast to the power deposition pattern of antenna 10 which remained essentially constant regardless of insertion depth (FIG. 2). In use, implanted antenna 17 is also entirely covered with a plastic catheter 16 (FIG. 1), closed at its distal end. The ordinates "% maximum temperature rise" in FIGS. 2 and 4 also depict "relative specific absorption rate."

DETAILED DESCRIPTION

The specific antenna embodiment 10 used for comparative testing purposes described below constituted a 0.095 cm OD semi-rigid coaxial cable sized to slip within plastic catheter 16 (FIG. 1). The outer diameters of inner conductor 11, insulator 12 and outer conductor 13 were 0.02 cm, 0.061 cm and 0.095 cm, respectively. Gap G, between the distal end of outer conductor 13 and the proximal end of helical coil 14, was 0.1 cm whereas length L of the helical coil was 1.0 cm. The distal end of the helical coil was soldered to the distal end of the inner conductor at 15. The inner and outer conductors were composed of a standard copper based alloy having high electromagnetic wave energy transmission properties whereas insulator 12 was composed of a standard Teflon (polytetraflouroethylene) material.

Helical coil 14 was also composed of a metallic conductor having high microwave energy transmission properties. For example, antennas constructed with 0.032 cm nichrome, 0.032 cm varnish insulated copper, and 0.0203 cm silver-plated copper wire all have been used successfully. The outside diameter of the helical coil closely approximated 0.12 cm to facilitate insertion of antenna 10 into standard 16-gauge plastic catheter 16.

Helical coil 14 was formed by wrapping a wire tightly around a stainless steel wire form, dimensioned to provide the desired diameter, length and turn density of helical coil 14. After extracting the wire form from the formed helical coil, the helical coil was installed carefully over the bare dielectric insulator portion of insulator 12, as shown in FIG. 1, and soldered at 15. Gap G was set at 0.1 cm.

In the preferred embodiments of this invention, axial length L and the turn density of helical coil 14 provide an impedance match of a microwave generator to an organic subject (e.g., tissue to be treated) at a microwave frequency ranging from approximately 0.1 to 3.0 GHz. Helical coil 14 preferably has a length L selected from the approximate range of from 1.0–10.0 cm and has equally spaced turns in the approximate range of 7 to 16 turns per cm. More sophisticated applications of this invention are anticipated with variable turn density along the coil to customize the heating field shape.

SURGICAL PROCEDURE

The following discussion briefly summarizes a typical surgical procedure using the above-described helical coil microwave antenna 10 for improving the localization of interstitial hyperthermia. An appropriate length antenna is first chosen to provide the desired heating pattern in accordance with the above discussions. For 915 MHz operation, a nichrome or copper wire coil with axial length L in the range of 1.0–10.0 cm may be selected for proper heat localization to the coil tip. Depending on target size, multiple-antenna array operation is possible to expand the effective heating volume.

A parallel array of 16-gauge plastic catheters 16 are inserted into the target region of a patient with the aid of a $\leq 1.0$ cm grid template or stereotactic surgical frame. Metal needles or stainless steel stylets are normally used to guide the catheters in place. A standard CT scan or simple X-ray will verify proper location of the catheters relative to the tumor or other tissue to be treated.

Antennas 10 are inserted into the desired catheters 16 and extended to the appropriate insertion depth. Standard temperature sensing probes are inserted into other plastic catheters to monitor and control the temperature distribution. If it is found that one or more of the antennas are not well matched electrically to the tissue load, minor adjustments can be made to the helical coil turn spacing or a double stub tuner can be used to obtain the best match of antenna to generator. Each antenna is connected to a microwave generator via a flexible coaxial cable in a conventional manner.

Microwave power can be controlled either manually or automatically by a computer feedback system to maintain the desired minimum tissue temperature (typically 43° C. for one hour, or equivalent). The temperature probes are manually translated inside the respective plastic catheters to monitor temperatures at approximately 1 cm increments within the heated tissue volume several times during the treatment to provide information on the internal temperature distribution of the tumor volume. At the end of treatment, microwave power is terminated and all antennas and sensors are removed from the catheters. Interstitial hyperthermia therapy induced via the implanted antennas can be repeated before and after radioactive seed brachyradiotherapy without additional surgery, using the same implanted plastic catheters 16.

COMPARATIVE EVALUATION WITH EXISTING TECHNOLOGY

Figure 3:
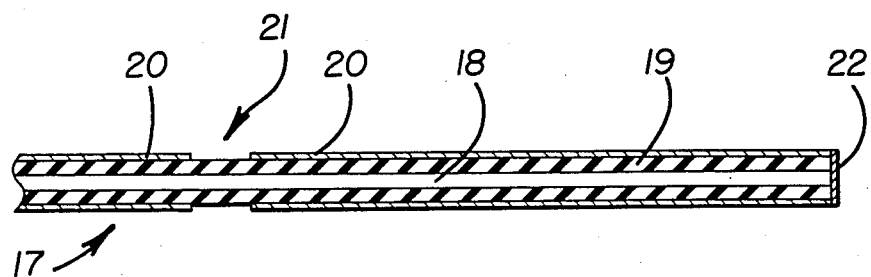
FIG. 3 is a longitudinal cross-sectional view of a commonly used style of implantable dipole antenna.

Standard dipole antenna 17 of FIG. 3 was constructed from a 0.095 cm semi-rigid coaxial cable having an inner conductor 18 covered by an insulator 19. An outer conductor 20 was cut circumferentially at 21 to form an axial separation gap of 0.1 cm between the cut portions of the outer insulator. A metallic connector 22 was soldered between the distal ends of the inner and outer conductors. Previous tests have shown this simple "Dipole" type structure operates identically to other dipole styles having a soldered connection (not shown in FIG. 3) of inner conductor 18 to outer conductor 20, adjacent to gap 21.

The specific polarization pattern of HCS style antennas is highly dependent on the source frequency, length of helix, spacing and diameter of coil turns 14.

Antenna 10 with a coil turn density of 10 turns/cm, a gap G of 0.1 cm, a coil diameter of 0.12 cm and a coil length of $\lambda/4$ of 1.0 cm (3.5 cm) was found to generate apparently circularly polarized electromagnetic waves which effectively localized the heating to the region surrounding the coil when driven at 2450 MHz (915 MHz). Other similar helical coil antennas with lengths L ranging from 1–5 cm, turn densities of 7–16 turns/cm and gap G from 0.1–5 cm also have been tested successfully at the two frequencies.

For comparative dosimetry study purposes and to match heating efficiencies of the antennas, each antenna was tuned to the coaxial feedline with a double stub tuner. The tuners were capable of precisely matching the antennas to the source frequency and feedline characteristics. This procedure enabled a direct comparison of antenna performance under optimum matched conditions, regardless of tissue properties or antenna insertion depth.

In order to study the antenna heating characteristics in a reproducible, homogenous tissue medium, soft tissue phantom was used initially to obtain the relative heating profiles of the different antenna configurations as a function of insertion depth. The phantom was composed of a mixture of distilled water (75.2%, base), TX-150 (15.4%, gelling agent), sodium chloride (1.0%, to adjust electrical conductivity), and polyethylene powder (8.4%, to lower dielectric constant). The mixture is known to have approximately the same electrical properties as those of human soft tissue at 915 MHz. A similarly appropriate phantom mixture was used for studies at 2450 MHz.

The material was contained in an $8 \times 8 \times 11$ cm plexiglass box transversed by a 0.5 cm array of 16-gauge Teflon catheters for holding the antennas and multi-sensor temperature probes. Five phantom models were constructed during the course of the experiments and the reproducibility of thermal profiles in each phantom was verified, using both antennas 10 and 17. To evaluate the difference in axial thermal profiles (FIG. 2 vs. FIG. 4) produced by each antenna type, single antennas were inserted into a catheter which was immersed in the phantom so that gap G (FIG. 1) or gap 21 (FIG. 3) was located 1.0 cm below the phantom surface. The total insertion depth of 2.1 cm (approximately $\lambda/2$ in tissue) was considered near optimum for the standard dipole antenna 17.

Figure 4:
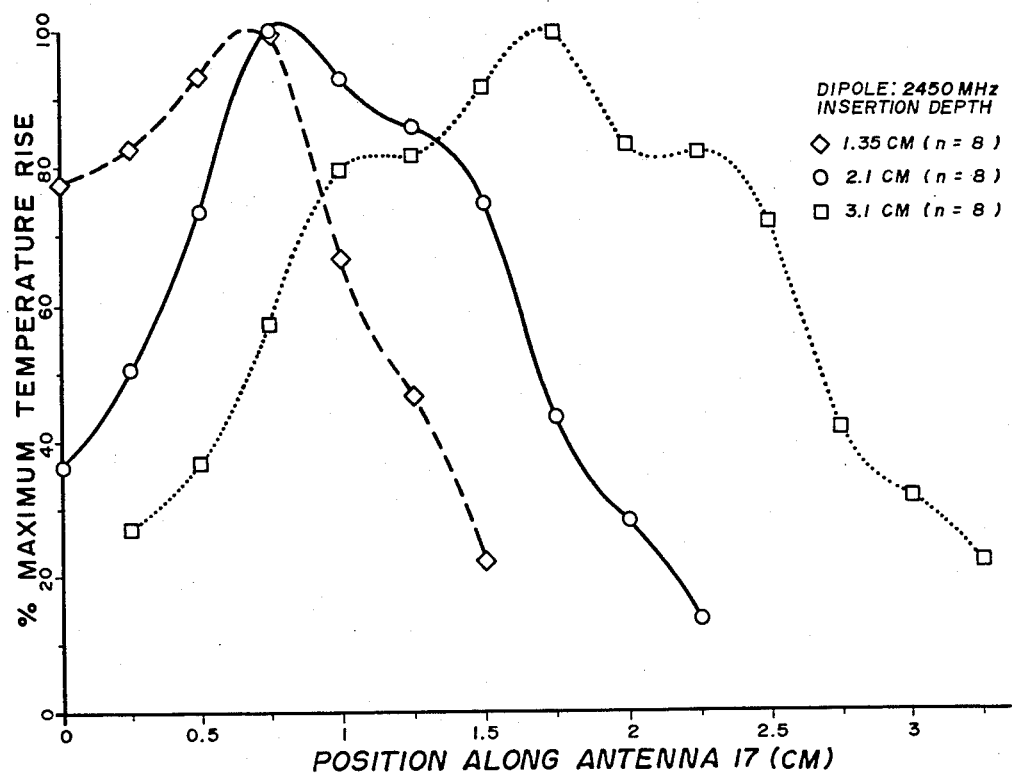
FIG. 4 is a graph, similar to FIG. 2, showing the effect of varying insertion depth on the axial thermal profiles of a 2450 MHz, L=1 cm simple dipole antenna (FIG. 3) for comparison with the antenna of this invention.

Axial power deposition profiles of antennas 10 and 17 were compared for total insertion depths of 1.35 cm, 2.1 cm and 3.1 cm in phantom, as illustrated by each of the three curves in FIGS. 2 and 4. These tests were intended to model the three clinically relevant conditions of antenna use: too shallow, optimum implant depth, and too deep. Radial power deposition profiles in several planes perpendicular to the antennas were obtained for a single insertion depth of 2.1 cm. These profiles were then compared to the radial temperature fall-off obtained using a heated water circuit of similar dimensions as a control for strictly thermal conduction heating.

The antennas were both driven at either 915 MHz or 2450 MHz using a continuous wave microwave power source (Model CA 2450, manufactured by Cheung Laboratory, Inc., Lanham-Seabrook, Md. Power fed to each antenna was tuned with a double stub tuner (Model 1729, Maury Microwave, Cucamonga, Calif.) for optimum impedance match to the generator, since no attempt was made to trim each antenna to exactly 50 ohms. Since the phantom material had no cooling effect from circulating blood, all experiments consisted of short 30 sec. heat trials during which the rate of change of temperature was determined at all internally monitored points to represent the power deposition characteristics of the antennas.

The thermal profile information was obtained using a multiple-sensor optical fiber probe with four sensors spaced 0.25 cm apart with each inserted in a catheter parallel to and 0.5 cm away from the antenna axis. Using a separate stationary single sensor probe located mid-depth in a second parallel catheter as control between trials, longer axial heating profiles were measured by moving the multi-sensor probe 1 cm and repeating the heat trial after cool-down of the phantom to initial conditions.

All temperatures were recorded every 10 seconds by a computerized fiber optic thermometry system and displayed in tabular and graphic forms on a color monitor. The increase in temperature above baseline [$\Delta T$ was calculated for each point and the measure of power deposition (Specific Absorption Rate or SAR) was determined from the time rate of change of temperature following power on as $SAR = c \cdot d\Delta T/dt$, wherein $c$ = specific heat of phantom tissue].

The axial thermal power deposition profile of each antenna was determined independently at four different sites within the phantom box for each experiment. The antennas were tested in more than one phantom to minimize erroneous conclusions that might arise from slight catheter placement variations at depth in the phantom or other systematic test errors. Axial profiles from corresponding trials were averaged together by first selecting the maximum SAR of each linear distribution as 100% SAR and normalizing the profile to a percentage of the peak (Relative SAR).

FIGS. 2 and 4 compare the effects of varying insertion depth on the axial power deposition profiles of antennas 10 and 17. As noted in FIG. 4, the thermal profile of standard antenna 17 varied significantly, depending on insertion depth. With a 3.1 cm total insertion depth, the thermal profile was almost symmetrical with the peak located 1.5 cm below the surface and a 50% HL and Dead Length of 2.04 and 0.68 cm, respectively. With a shorter insertion of 1.35 cm (gap 21 depth of 0.25 cm), the 50% HL and Dead Lengths were both drastically reduced to 1.21 cm and 0.17 cm, respectively, but the antenna entrance point was overheated with 78% of the peak SAR obtained near the surface.

In contrast, the power deposition profiles induced by antenna 10 were essentially identical regardless of insertion depth. The heat peak moved correspondingly deeper with increasing insertion, remaining 0.5 cm proximal to the antenna tip midway along the axis of helical coil 14 (FIG. 1). The 50% HL for 1.35, 2.1, and 3.1 cm insertion depths was a constant 1.2 cm and the Dead Length remained essentially 0.0. Studies on the reproducibility of profiles for antennas 10 and 17 tested identically in five different phantoms disclosed no significant variation in the location of Peak Depth, 50% HL, or Dead Length.

Figure 5:
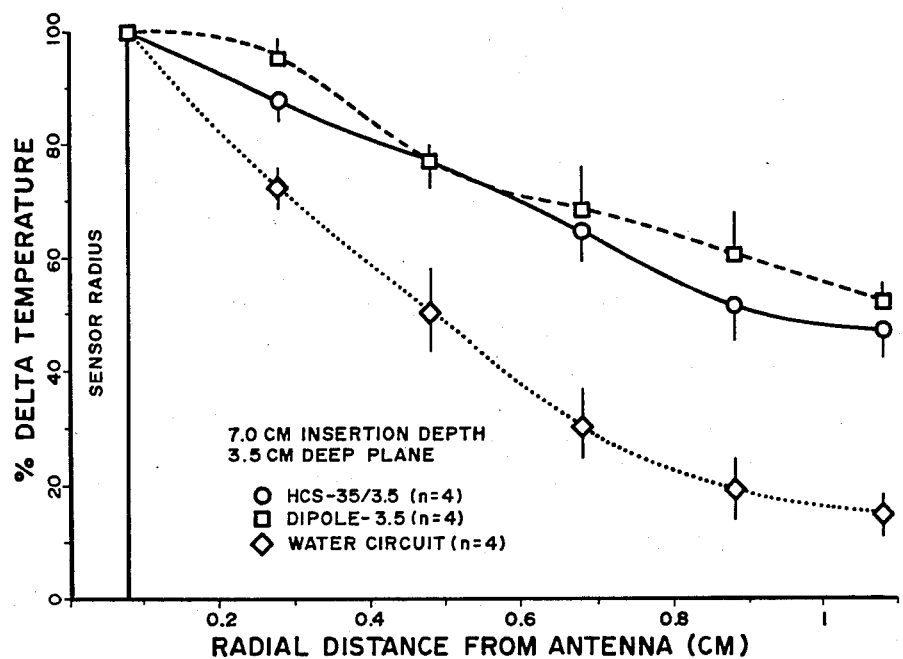
FIG. 5 is a comparison in dog thigh muscle in vivo of the radial temperature fall-off from the antenna of this invention to that of the standard dipole antenna, and to that of thermal conduction heating only.
Figure 6:
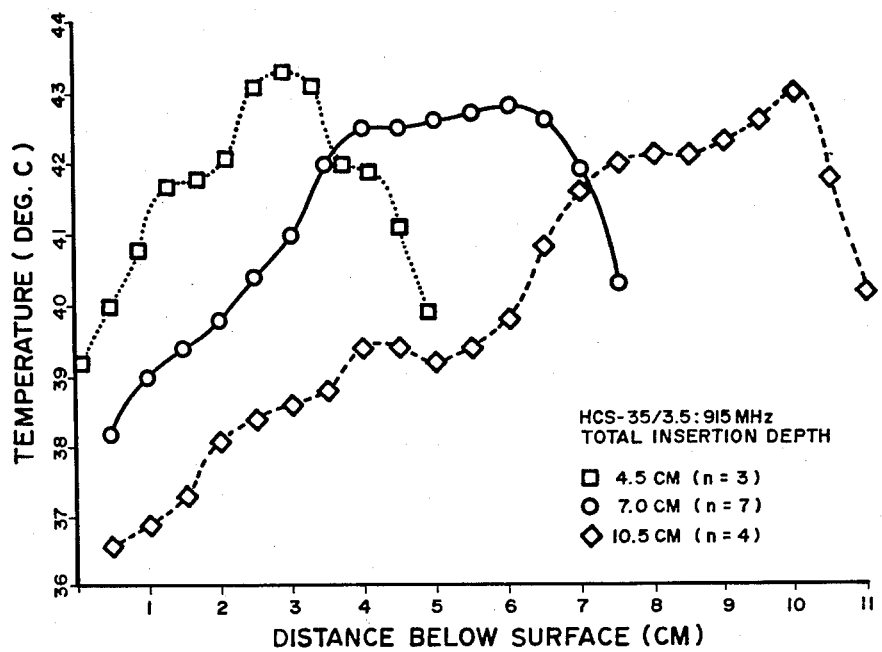
FIG. 6 is a graph showing the essentially constant shape of the induced temperature distribution for three different 915 MHz helical coil antenna insertion depths in dog thigh muscle in vivo.

Relative radial power deposition profiles perpendicular to the axes of antennas 10 and 17 were also obtained and compared with the radial temperature fall-off from a heated water circuit of similar dimensions. The corresponding comparative radial temperature distributions for L=3.5 cm antennas 10 and 17 driven at 915 MHz in dog thigh muscle tissue in vivo are shown in FIG. 5. FIG. 6 gives the absolute temperature distributions in dog thigh muscle along the axial length of antenna 10 (at R=0.5 cm distance) for three different clinically relevant antenna insertion depths. Note the very similar 50% HL's and slopes of the individual temperature distributions for the three different implant conditions.

We claim:

1. An implantable helical coil microwave antenna for improving localization of interstitial hyperthermia comprising
   an inner conductor,
   a dielectric insulator covering said inner conductor,
   an outer conductor covering only a proximal portion of said insulator to form a coaxial cable thereat and to leave a distal portion of said insulator uncovered, and
   a helical coil means surrounding the distal portion of said insulator and having a proximal end spaced axially from a distal end of said outer conductor to form a separation gap therebetween and a distal end of said coil means connected to a distal end of said inner conductor for confining heat to immediate areas surrounding said coil means and for inducing substantially identical thermal profiles at varying depths of insertion of said antenna into an organic subject when said antenna is energized with microwave energy.

2. The antenna of claim 1 wherein the axial length and turn density of said helical coil means provide an impedance match of a microwave generator to said organic subject at a microwave frequency within the range of 0.1 to 3.0 GHz.

3. The antenna of claim 1 wherein the outside diameter of of said helical coil means is constant.

4. The antenna of claim 3 wherein the outside diameter of said outer conductor approximates 0.095 cm for close insertion within a 16-gauge catheter.

5. The antenna of claim 3 wherein the outside diameter of said coil means approximates 0.12 cm.

6. The antenna of claim 1 or 5 wherein said helical coil means has a length selected from the approximate range of from 1.0 to 20.0 cm and has turns in the approximate range of from 7 to 16 turns per cm of said length.

7. The antenna of claim 1 or 5 wherein the separation gap between the proximal end of said helical coil means and the distal end of said outer conductor has a length in the approximate range of from 0.1 cm to 5.0 cm.

8. The antenna of claim 7 wherein said helical coil means comprises a metallic wire coiled to have at least seven turns per cm of axial length thereof.

9. The antenna of claim 8 wherein said wire has ten turns per cm of axial length thereof.

10. The antenna of claim 8 wherein the outside diameter of said wire is selected from the approximate range of from 0.02 to 0.04 cm.

11. The antenna of claim 10 wherein said wire is composed of nichrome, bare copper, varnish insulated copper or silver-plated copper.

12. The antenna of claim 1 wherein the outside diameter of said helical coil means varies.

* * * * *